(12) United States Patent
Hails et al.

(10) Patent No.: US 8,741,151 B2
(45) Date of Patent: Jun. 3, 2014

(54) ANALYSIS OF POLYMERIC SCALE INHIBITORS

(75) Inventors: Mike Hails, Worchester (GB); Chris Jones, Cheslyn Hay (GB)

(73) Assignee: Rhodia UK Limited, Watford Hertfordshire (GB)

( * ) Notice: Subject to any disclaimer, the term of this patent is extended or adjusted under 35 U.S.C. 154(b) by 1375 days.

(21) Appl. No.: 11/887,929

(22) PCT Filed: Apr. 4, 2006

(86) PCT No.: PCT/EP2006/061291
§ 371 (c)(1),
(2), (4) Date: Nov. 3, 2008

(87) PCT Pub. No.: WO2006/106099
PCT Pub. Date: Oct. 12, 2006

(65) Prior Publication Data
US 2009/0065433 A1 Mar. 12, 2009

(30) Foreign Application Priority Data
Apr. 6, 2005 (GB) .................................. 0506962.0

(51) Int. Cl.
*B01D 15/36* (2006.01)
*C02F 5/00* (2006.01)
*C02F 5/10* (2006.01)
*C02F 5/14* (2006.01)

(52) U.S. Cl.
USPC ...... 210/696; 73/61.43; 73/61.52; 73/152.18; 73/152.23; 210/656; 210/698; 210/699; 210/747.5; 422/14; 422/15; 422/16; 436/104; 436/127; 436/161

(58) Field of Classification Search
USPC ......... 210/638, 639, 656, 679, 681, 683, 685, 210/691, 696–700, 747.5; 436/25, 30, 103, 436/104, 119, 120, 161; 73/61.43, 61.52, 73/61.53, 152.01, 152.18, 152.23, 152.24, 73/152.43; 422/14–16
See application file for complete search history.

(56) References Cited

U.S. PATENT DOCUMENTS

| | | | | |
|---|---|---|---|---|
| 3,488,922 A | * | 1/1970 | Kirkland | 95/88 |
| 3,827,977 A | * | 8/1974 | Miles et al. | 507/225 |
| 3,956,179 A | * | 5/1976 | Sebastian et al. | 502/158 |
| 4,115,261 A | | 9/1978 | Corte et al. | |
| 4,514,504 A | * | 4/1985 | Rothman | 436/85 |
| 4,544,639 A | * | 10/1985 | Faust | 436/104 |
| 5,032,266 A | * | 7/1991 | Kirkland et al. | 210/198.2 |
| 5,152,177 A | * | 10/1992 | Buck et al. | 73/61.54 |
| 5,288,410 A | * | 2/1994 | Cuisia | 210/699 |
| 5,300,231 A | * | 4/1994 | Cha | 210/700 |
| 6,316,647 B1 | * | 11/2001 | Ohtsu et al. | 554/194 |
| 6,656,365 B2 | * | 12/2003 | Suzuki et al. | 210/701 |
| 2004/0135125 A1 | * | 7/2004 | Morris et al. | 252/408.1 |
| 2006/0032816 A1 | * | 2/2006 | Marcus et al. | 210/634 |

FOREIGN PATENT DOCUMENTS

| | | |
|---|---|---|
| EP | 0 320 023 B1 | 6/1989 |
| GB | 2213933 * | 8/1989 |
| WO | WO 99/64480 A1 | 12/1999 |

* cited by examiner

*Primary Examiner* — Joseph Drodge
(74) *Attorney, Agent, or Firm* — Dentons US LLP

(57) ABSTRACT

The scale inhibitors in a variety of aqueous systems, or a part or sample thereof, also including one or more dissolved interfering ions, are separated therefrom and analyzed, such scale inhibitors comprising a polymer containing at least one anionic functional group, e.g., a strong acid functional group or a phosphonate or phosphate ester, and such analysis including treating these aqueous systems with a cationic substrate or a free cation.

20 Claims, No Drawings

ANALYSIS OF POLYMERIC SCALE INHIBITORS

CROSS-REFERENCE TO PRIORITY APPLICATIONS

This application is the United States national phase of International Application No. PCT/EP 2006/061291, filed Apr. 4, 2006, published in French as International Publication No. WO 2006/106099 A1 on Oct. 12, 2006, and claims priority of Great Britain Application No. 0506962.0, filed Apr. 6, 2005, each hereby expressly incorporated by reference in its entirety and each assigned to the assignee hereof.

The present invention relates to a method of analyzing and monitoring scale inhibitor content in the presence of interfering ions. In particular, the scale inhibitors to be analyzed or monitored are polymeric and include an anionic group, such as a strong acidic group, however, they may alternatively comprise phosphonates or phosphate esters.

In most aqueous systems used in industry, such as in cooling towers, in boilers and in or as formation fluids and production fluids for oil and gas extraction, problems are caused by the formation and deposition of scales. The scales commonly encountered include calcium carbonate, calcium sulfate, barium sulfate, magnesium carbonate, magnesium hydroxide, strontium carbonate and strontium sulfate. The scales formed and deposited can lead to the plugging of pipes and bores, the sticking of valves and the damage or hindrance of equipment, particularly that with moving parts.

As a result of the problems caused by scale formation and deposition aqueous systems used in industry are generally treated with one or more scale inhibitors. The level of scale inhibitor present in the aqueous system must be kept at or above a predetermined level, the minimum inhibitory concentration (MIC), in the aqueous system in order that scale formation and deposition is prevented.

To maximize the efficiency of any scale inhibitor treatment, it is desirable to be able to accurately monitor the level of scale inhibitor present in the aqueous system, so that an unnecessary excess or re-application of scale inhibitor is avoided. For example, in the extraction of oil or gas from underground supplies, scale inhibitors are typically deployed as part of a "squeeze treatment," whereby the scale inhibitor is pumped down the production well as a concentrated solution and is absorbed onto the rock substrate. As production from the treated well recommences, the inhibitor is released from the rock and is available to control scaling within the production well bore and production tubing/well. There is the need for a particular level (MIC) of scale inhibitor for scale formation and deposition to be prevented but it is also desirable to delay reapplying the scale inhibitor for as long as possible, i.e., obtaining a long "squeeze lifetime" since treatments are expensive in terms of logistics and deferred oil production.

To enable long or extended squeeze lifetimes to be obtained, it is essential to be able to accurately detect the presence of the scale inhibitor in the produced fluids at low concentrations equating to the "MIC region." In practice, this will vary from one oil/gas field to another, but typically may result in a need to detect inhibitors at levels as low as 1 ppm in concentrated brine solutions, in either produced water or formation water.

Within the oil industry, new oil fields are being exploited that are more severe than historical fields in terms of both "downhole" temperatures and increased salinity. To combat scale deposition in such oil fields, new scale inhibitors have been developed that are compatible with the environments of these fields and are capable of controlling scale at concentrations as low as 1 ppm.

Such scale inhibitors typically comprise polymers having anionic groups and in particular polymers having strong acidic groups, such as polymers including sulfur containing monomers or phosphorus containing monomers. Alternatively, the scale inhibitors may comprise phosphonates or phosphate esters, These types of inhibitors display good inhibition of scales including barium sulfur and calcium carbonate and can, in some cases, be used at lower levels than other known inhibitors. For ease of reference, the phrase "polymers including at least one anionic group" should be understood as including phosphonates, phosphate esters and polymers including at least one anionic group, particularly polymers including at least one strong acidic group.

There are in existence several techniques used to determine the level of scale inhibitor in an aqueous system. However, dissolved ions, particularly anions such as chloride ions, cations such as calcium and high salinity in general can all interfere with the reactions on which these techniques are based and one or more must be removed before the level of inhibitor can be determined.

For polyacrylate based scale inhibitors, separation of the inhibitor from the dissolved ions can be achieved by the use of reverse phase chromatographic cartridges with a C18 (octadecylsilane) bonded stationary phase. Using such systems, the polyacrylate can, by careful pH control, be retained on the C18 phase and therefore this offers a mechanism of separating the polymer from the system water including the dissolved interfering ions. However, polymers having strong acidic groups, such as sulfonic and/or phosphonic groups cannot be retained on such substrates and so can't easily be separated from the dissolved interfering ions and, therefore, can't easily be detected in the system water.

Accordingly, there remains a need for a procedure to separate an inhibitor having anionic groups, and in particular strongly acidic groups, from dissolved interfering ions. The level of inhibitor can then be determined by a variety of existing analytical techniques once the interfering ions have been removed.

Accordingly, in a first aspect, the present invention provides a method for treating an aqueous system, or a part or sample thereof, including a scale inhibitor and one or more dissolved interfering ions to separate the scale inhibitor from the aqueous system and the dissolved interfering ions, wherein the scale inhibitor comprises a polymer including at least one anionic group and the method comprises treating the aqueous system with a cationic substrate.

The method allows treating of an aqueous system, or a part or sample thereof, to separate the scale inhibitor from the system water and dissolved interfering ions to enable accurate and low level analysis of the scale inhibitor to occur. The use of a cationic substrate retains the scale inhibitor and allows passage of the system water. The method is particularly advantageous for use on samples of an aqueous system before the sample is analysed for scale inhibitor level.

Hereinafter the phrase "aqueous system" should be taken to include an aqueous system, or a part or a sample thereof.

The aqueous system may be from, or part of, a cooling tower or boiler or, more preferably may comprise processing or producing aqueous solutions/fluids with high levels of dissolved ions, i.e. high salinity. Such fluids are typically encountered during oil production/extraction, in the form of seawater, formation water or produced water, or during geothermal energy production or during the desalination of either seawater or brackish water.

Accordingly, in a second aspect, the present invention provides a method for treating seawater, formation water or produced water, or a part or sample thereof, encountered during oil/gas production/extraction processes and including a scale inhibitor and one or more dissolved interfering ions to separate the scale inhibitor from the seawater, formation water or produced water to remove the dissolved interfering ions to enable accurate and low level analysis of the scale inhibitor to occur, wherein the scale inhibitor comprises a polymer including at least one anionic group and the method comprises treating the seawater, formation water or produced water with a cationic substrate.

Preferably, the scale inhibitor comprises a polymer including at least one strong acidic group.

More preferably, the scale inhibitor comprises a polymer including at least one sulfur containing monomer and/or at least one phosphorus containing monomer.

Most preferred sulfur containing monomers include vinyl sulfonates, 2-acrylamido-2-methylpropane sulfonic acid (AMPS) and allyl sulfonates.

Preferred phosphorus containing monomers include vinyl phosphonic acid (VPA), vinylidene diphosphonic acid (VDPA), hypophosphorous acid and phosphorus acid.

A most preferred polymer including at least one anionic group is a polymer of VDA/VDPA and a vinyl sulfonate or an allyl sulfonate.

Preferably, the cationic substrate is a substrate having attached an amine group. Preferably, the amine group is an alkylamine, most preferably a propylamine.

Preferably, the substrate having an amine group attached is one or more silica bead, one or more polymer bead or a mixture thereof. In particular, commercially available solid phase extraction (SPE) products including an amine group may be used. More preferably, the substrate having an amine group attached is a reverse phase chromatographic cartridge.

Most preferably, the cationic substrate is an amine functionalized substrate, such as a propylamine functionalized silica substrate, in particular a commercially available solid phase extraction (SPE) product. However, the method will also work if the chosen amine is used in a "free" form without any supporting substrate.

The aqueous solution is preferably acidified and passed through the solid phase extraction product. The result of this treatment step is the attachment of the scale inhibitor to the protonated cationic, preferably amine, group of the substrate that effectively retains the inhibitor on the substrate as the system water passes through or over the substrate without being retained. Thus, the inhibitor is separated from the aqueous system containing the dissolved interfering ions.

The scale inhibitor is then eluted from the cartridge by the passing of a basic solution through the cartridge, which deprotonates the cationic group allowing the anionic scale inhibitor to be released.

The relative volumes of the acidified sample and basic solution can be adjusted to dilute or concentrate the sample to aid analysis, in particular to improve the accuracy and precision at lower levels or indeed to reduce the limit of detection below that normally available for the analytical procedure employed.

The resultant eluent containing the scale inhibitor but no system water or dissolved interfering ions can then be analyzed by a variety of known techniques. Suitable known analysis techniques include, but are not limited to, the use of colorimetric techniques such as pinacyanol chloride dye and ammonium phosphonomolybdate or turbimetric techniques such as the use of Hyamine® 1622 (a quaternary ammonium salt), each of which interact with the scale inhibitor, to give rise to a complex that can be quantitatively analyzed. These interactions are masked by high levels of dissolved interfering ions and hence are either problematic or not possible without separation of the scale inhibitor from saline fluids.

According to a third aspect, the present invention provides the use of an alkylamine, preferably a propylamine, solid phase extraction (SPE) product in the separation of a scale inhibitor from an aqueous system containing dissolved interfering ions, e.g. brines, wherein the scale inhibitor comprises a polymer including at least one anionic group.

The present invention is extremely advantageous as it allows the analysis of levels of scale inhibitors comprising polymers including at least one anionic group by successfully separating the polymer including at least one anionic group from dissolved ions that interfere with analysis techniques. Prior to the present invention, it was not possible to separate certain polymers including at least one anionic group, particularly sulfonated groups, from dissolved interfering ions and so analysis of the level of the polymer, dosed into, for example a saline fluid, was either problematic or not possible at low concentrations.

In particular, the present invention is advantageous in the extraction/production of oil and gas from underground supplies as it allows the level of scale inhibitor used in a squeeze treatment to be accurately monitored. This is particularly important in oil/gas reservoirs where the MIC is low and, for a prolonged period of time, there is a need to accurately detect scale inhibitors in brines (produced water or formation water) at low concentrations.

The preferred types of scale inhibitor for use in the extraction of oil and gas comprise polymers including at least one sulfur containing monomer and/or at least one phosphorus containing monomer. The latter type of scale inhibitors are relatively new and may either be effective at much lower concentrations than previously available scale inhibitors or compatible with systems that previously available scale inhibitors are not compatible with. In either case, there is an increasing need to be able to detect such polymers at lower concentrations in fluids/waters having, for example, increased salinity.

As the current scale inhibitors work at such a low concentration there is a need in the industry to be able to analyze the presence of the scale inhibitor in the system with a great degree of accuracy. Owing to the interference of dissolved ions present in many aqueous systems, it was previously only possible to analyze such polymers down to a level of approximately 50 ppm. As a more accurate analysis was not possible, it had to be assumed that when the level of scale inhibitor dropped to 50 ppm it was necessary to reapply the scale inhibitor. This could lead to the need to carry out unnecessary squeeze treatments at significant cost to an oil operator due to the logistics of the process and deferred oil production, particularly if the MIC for the polymer in a given system was known to be below 50 ppm.

The current scale inhibitors comprising a polymer including at least one sulfur containing monomer and/or at least one phosphorus containing monomer can be used at levels as low as 1 ppm to prevent the formation and deposition of scale, with the exact MIC depending upon specific water and system characteristics. Accordingly, being able to analyze the scale inhibitor level with this degree of accuracy means that it is not necessary to reapply the scale inhibitor when the level reaches 50 ppm but this can be deferred until the MIC level is reached, thus potentially greatly extending the life of the squeeze treatment.

In a further aspect of the current invention, there is provided a method of treating an aqueous system, or part or sample thereof, including a scale inhibitor comprising a polymer including at least one anionic group and one or more further scale inhibitors and one or more dissolved interfering ions to separate the scale inhibitors from the aqueous system and the dissolved ions and from each other to allow accurate and low level analysis of the scale inhibitors to occur, the method comprising, in any order:

a) carrying out a treatment step to remove the one or more further scale inhibitor from the aqueous system; and b) treating the aqueous system with a cationic substrate to retain the polymer comprising at least one anionic group.

Step a) may comprise use of a conventional C-18 functionalized substrate.

For example, an aqueous system including a polyacrylate scale inhibitor, a polyvinylsulfonate (PVSA) scale inhibitor and a VDPA/vinylsulfonate copolymer scale inhibitor together with dissolved interfering ions can be separated and detected as follows:

Upon passage of the aqueous system through a C-18 substrate, the polyacrylate scale inhibitor is retained other polymers pass through with the dissolved interfering ions. The polyacrylate scale inhibitor can be removed from the C-18 substrate and detected by hyamine analysis.

The eluent containing the polyvinylsulfonate (PVSA) scale inhibitor and the VDPA/vinylsulfonate copolymer scale inhibitor is then passed through a cationic, preferably amine, functionalized substrate and both polymers are retained on the substrate and therefore separated from the dissolved interfering ions. The polymers are then removed from the substrate and separately detected by using hyamine analysis for the PVSA scale inhibitor and ammonium phosphonomolybdate for the VDPA/vinylsulfonate copolymer scale inhibitor.

The invention claimed is:

1. A method for treating an aqueous system comprising a scale inhibitor and one or more dissolved interfering ions, wherein said scale inhibitor comprises at least one polymer containing at least one anionic functional group and said scale inhibitor being different from a polyacrylate based scale inhibitor, said method comprising separating the scale inhibitor from the aqueous system, or part or sample thereof, and the dissolved interfering ions, which interfere with analysis of the level of scale inhibitor, by treating the aqueous system, or part or sample thereof, with a cationic substrate or a free cation, and then analyzing the scale inhibitor level.

2. The method as defined by claim 1, wherein the aqueous system is from, or part of, a cooling tower or boiler.

3. The method as defined by claim 1, wherein the scale inhibitor comprises a polymer containing at least one strong acidic functional group.

4. The method as defined by claim 3, wherein the scale inhibitor comprises a polymer containing at least one sulfur containing monomer and/or at least one phosphorus containing monomer.

5. The method as defined by claim 4, said scale inhibitor comprising a polymer comprising a sulfur containing monomer which comprises a vinyl sulfonate, 2-acrylamido-2-methylpropane sulfonic acid (AMPS) or an allyl sulfonate.

6. The method as defined by claim 4, said scale inhibitor comprising a polymer comprising a phosphorus containing monomer which comprises vinyl phosphonic acid (VPA), vinylidene diphosphonic acid (VDPA), hypophosphorous acid or phosphorus acid.

7. The method as defined by claim 1, wherein said polymer containing at least one anionic functional group is a polymer of VPA/VDPA and a vinyl sulfonate or an allyl sulfonate.

8. The method as defined by claim 1, wherein the scale inhibitor comprises a phosphonate or a phosphate ester.

9. The method as defined by claim 1, wherein the cationic substrate comprises a substrate having an amine group attached thereto.

10. The method as defined by claim 9, wherein said amine group comprises a propylamine.

11. The method as defined by claim 9, wherein said substrate having an amine group attached thereto comprises one or more silica beads, one or more polymer beads or a mixture thereof.

12. The method as defined by claim 11, wherein said substrate having an amine group attached thereto comprises a propylamine functionalized silica substrate.

13. The method as defined by claim 1, comprising treating the aqueous system with a free cation which comprises a free amine group.

14. The method as defined by claim 1, comprising treating the aqueous system with a cationic substrate by utilizing a reverse phase chromatographic cartridge.

15. A method for treating seawater, formation water or produced water encountered during oil or gas production or extraction processes comprising a scale inhibitor and one or more dissolved interfering ions, which interfere with analysis of the level of scale inhibitor, wherein said scale inhibitor comprises at least one polymer containing at least one anionic functional group and said scale inhibitor being different from a polyacrylate based scale inhibitor, said method comprising separating the scale inhibitor from the seawater, formation water or produced water by treating the seawater, formation water or produced water with a cationic substrate or a free cation, and then analyzing the scale inhibitor level.

16. A method for treating an aqueous system comprising at least one first scale inhibitor and one or more dissolved interfering ions, wherein said scale inhibitor comprises a polymer containing at least one anionic functional group wherein said first scale inhibitor is different from a polyacrylate based scale inhibitor, and one or more additional scale inhibitors and one or more dissolved interfering ions to separate the first and additional scale inhibitors from the aqueous system, or part or sample thereof, and the dissolved ions and from each other to permit accurate and low level analysis of the first and additional scale inhibitors, said method comprising, in any order:

a) removing the one or more additional scale inhibitors from the aqueous system, or part or sample thereof; and b) treating the aqueous system, or part or sample thereof, with a cationic substrate or a free cation to retain said first scale inhibitor comprising the polymer containing at least one anionic functional group.

17. The method as defined by claim 16, wherein step b) comprises treating with a C-18 functionalized substrate.

18. The method as defined by claim 16, wherein the at least one additional scale inhibitor comprises a polyacrylate based scale inhibitor.

19. A method for treating an aqueous system comprising at least one scale inhibitor comprising a polymer comprising a sulfur containing monomer and one or more dissolved interfering ions, wherein said scale inhibitor is different from a polyacrylate based scale inhibitor, said method comprising treating the aqueous system, or part sample thereof, with a cationic substrate or a free cation to separate said scale inhibitor from the aqueous system and the dissolved interfering ions.

20. A method for analyzing and monitoring the amount of at least one scale inhibitor in an aqueous system comprising one or more dissolved interfering ions including chloride and calcium ions, wherein said scale inhibitor comprises a polymer comprising strong acidic groups, and said scale inhibitor is different from a polyacrylate scale inhibitor, said method comprising: (i) separating said scale inhibitor from the aqueous system, or part or sample thereof, and said dissolved interfering ions by treating said aqueous system, or a part or sample thereof, with a cationic substrate or a free cation; (ii) analyzing the amount of said scale inhibitor separated from the aqueous system, or part or sample thereof; and (iii) monitoring the amount of said scale inhibitor in the aqueous system, or part or sample thereof, to keep it above the Minimum Inhibitory Concentration (MIC).

* * * * *